US006366353B1

(12) United States Patent
Brown et al.

(10) Patent No.: US 6,366,353 B1
(45) Date of Patent: Apr. 2, 2002

(54) METHOD TO DETERMINE THE IDENTITY OF A MATERIAL IN AN OBJECT

(75) Inventors: John T. Brown, Corning; Xiaodong Fu, Painted Post; Mahendra K. Misra, Horseheads; Frederic J-Y Quan, Corning, all of NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/434,700

(22) Filed: Nov. 5, 1999

(51) Int. Cl.[7] .............................................. G01N 21/63
(52) U.S. Cl. ....................................................... 356/318
(58) Field of Search .................................. 356/317, 318

(56) References Cited

U.S. PATENT DOCUMENTS

| 4,637,938 A | 1/1987 | Lee et al. |
| 5,751,416 A | 5/1998 | Cook et al. |
| 5,847,825 A | 12/1998 | Alexander |
| 6,128,928 A | * 10/2000 | Antos et al. ................... 65/421 |

FOREIGN PATENT DOCUMENTS

| DE | 40 26 371 | 2/1992 |
| EP | 0 299 752 | 1/1989 |
| JP | 7-33468 A | * 2/1995 |
| JP | 8-94526 A | * 4/1996 |

OTHER PUBLICATIONS

David K. Ottesen, "The Detection of Contaminants on Electronic Microcircuit Substrates by Laser Spark Emission Spectroscopy", Sandia Report, Dec. 1991, pp. 9–16.

* cited by examiner

Primary Examiner—F. L. Evans
(74) Attorney, Agent, or Firm—Timothy R. Krogh

(57) ABSTRACT

A method and apparatus for determining an identity of at least one constituent on a soot that is deposited on a substrate is disclosed. The method includes the steps of sending a pulse of energy toward the substrate, focusing the energy to a predetermined point on the substrate to thereby generate a plasma on the substrate and to create at least one photon, detecting the photon using an analysis element, and identifying the constituent in the soot. The method may also include the step of determining the concentration of the constituent. Furthermore, the method may be used to determine the identity and concentration of at least one reactant in a flame of a burner or a reactant stream.

28 Claims, 4 Drawing Sheets

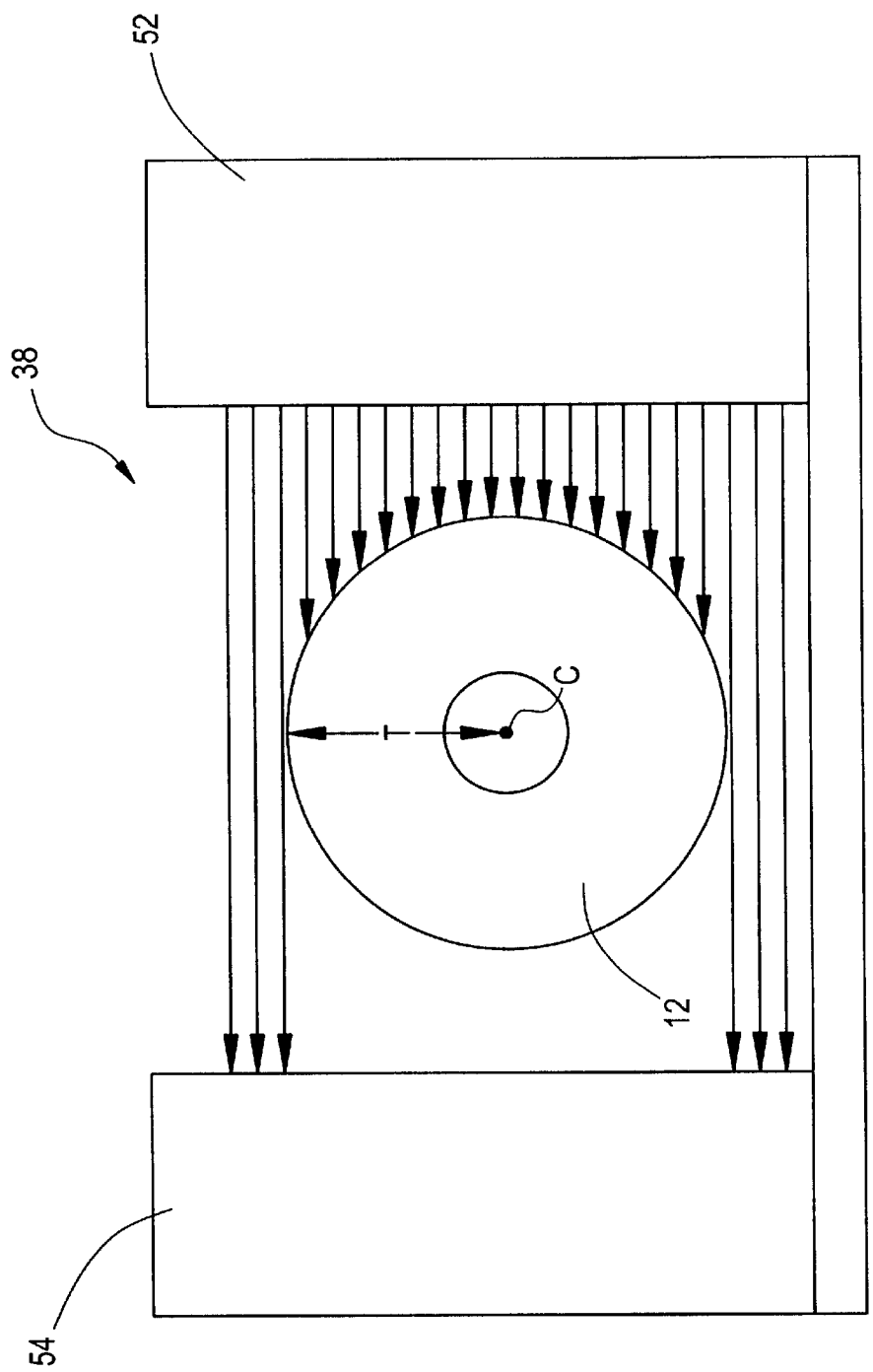

METHOD TO DETERMINE THE IDENTITY OF A MATERIAL IN AN OBJECT

BACKGROUND OF THE INVENTION

1. Field of the Invention

The present invention relates to a method and an apparatus using laser induced breakdown spectroscopy ("LIBS") to identify a constituent in a process to produce a soot and to determine the amount of the constituent. More specifically, the present invention relates to a method and an apparatus using photon emissions to identify the constituent and to determine the amount of the constituent in a soot formed from a chemical vapor deposition ("CVD") process to produce a product such as an optical waveguide fiber ("optical fiber"). The invention may also be used to identify a constituent and its concentration level in a flame of a deposition burner for applying the soot to a substrate. The invention may further be used to determine a constituent and its concentration in a reaction stream or on a solid surface.

2. Technical Background

In a CVD process, a particulate is formed and deposited on a substrate. CVD processes may be used in the manufacturing of various products. CVD techniques may be used to apply coatings to glazings as well as other types of substrates. CVD technology may also be used to form glass articles such as photolithography lenses, optical fibers, and photonic amplifiers.

The optical fiber typically includes a cladding made of pure silica ($SiO_2$) and a core made of silica doped with germanium dioxide ($GeO_2$) or some other index of refraction modifying dopant. The dopant alters the refractive index of the silica in the core or cladding creating structures to funnel light. Portions of the core often contain different concentrations of germanium, fluorine, phosphorus, titanium oxide, or other dopants, resulting in different refractive indexes along the diameter of the core. The distribution of refractive indexes along the diameter of the core (i.e., the refractive-index profile) determines operating characteristics of the optical fiber.

A conventional process known as outside vapor deposition ("OVD") can be used to form the optical fiber. Generally, the OVD process involves forming a soot preform by burning a gaseous mixture to produce soot containing silica and at least one dopant, such as germanium dioxide. Layers of the soot are successively deposited onto a mandrel to form a core portion of the soot preform.

A cladding is formed on the core portion by burning a gaseous mixture to produce soot containing silica and index reducing or increasing dopants, and successively depositing layers of that soot onto the core portion. The soot preform is consolidated by sintering the preform to form a glass blank. An optical fiber is drawn from the glass blank. The concentrations of dopant in the soot layers forming the fiber primarily determine the concentrations of dopant along the diameter of the resulting optical fiber.

It would be desirable to measure the concentrations of the dopant in the soot layers to determine if the soot preform can be expected to produce an optical fiber with a desired refractive-index profile. Currently, the concentration of the dopant of the soot preform is measured off-line. The off-line process is typically expensive and time consuming. Off-line processes also include many handling steps, which may introduce a significant source of contamination, loss of product, and/or sampling errors. Also, off-line measurements cannot be used to control on-line processing.

Also, controlling the refractive index profile of the optical waveguide fiber is mandatory for commercial fiber designs. This is especially the case for complex refractive index profile fibers. The traditional manufacturing processes of producing optical fiber have new challenges in terms of the precision requirements of the deposition of the soot, the consolidation, and the draw. An on-line method, which could identify the constituents in the preform, either the dopants or the silica, and also determine the concentration of each constituent is desired.

SUMMARY OF THE INVENTION

One aspect of the present invention includes a method of determining the identity of a constituent and/or its concentration level in a soot deposited on a soot coated substrate. The method includes the steps of sending a pulse of energy toward the coated substrate, focusing the energy to a predetermined point on the substrate to thereby generate a plasma on the substrate and to create at least one photon, detecting the photon using an analysis element, and identifying the constituent or its amount in the soot.

Another aspect of the invention includes a method for determining the identity and/or concentration of at least one reactant in the flame of a chemical vapor deposition process for depositing a soot on a substrate. The method includes the steps of sending a pulse of energy toward the flame, focusing the energy to a predetermined point in the flame to thereby generate a plasma in the flame and to create at least one photon, detecting the photon using an analysis element, and identifying the constituent or its amount in the flame.

A further aspect of the invention includes a method of controlling the manufacture of the soot deposited on the substrate. The method includes the steps of sending a pulse of energy toward a substrate, focusing the energy to a predetermined point on the substrate to thereby generate a plasma on the substrate and to create at least one photon, detecting the photon using an analysis element, and determining the identity or amount of the constituent in the soot, comparing the identity or amount of the constituent to a predetermined set of parameters, and adjusting at least one reaction condition such that the identity or amount of the constituent will be altered to match at least one of the predetermined set of parameters.

An additional aspect of the invention includes a soot coated substrate made from a process comprising the steps of depositing a soot on a substrate, sending a pulse of energy toward the coated substrate, focusing the energy to a predetermined point on the substrate to thereby generate a plasma on the substrate and to create at least one photon, detecting the photon using an analysis element, and determining the identity on amount of the constituent in the soot.

Yet another aspect of the present invention includes a method for determining the diameter or thickness of the substrate. The method includes the steps of sending a pulse of energy toward a substrate, focusing the energy to a predetermined point on the substrate to thereby generate a plasma on the substrate and to create at least one photon, detecting the photon using an analysis element, identifying the constituent and its amount in the soot, and measuring the thickness of the substrate.

An additional aspect of this invention may include utilizing the laser induced breakdown spectroscopy technique of using a laser to create a plasma and thereby generate photons to identify elements and their concentrations. This may be incorporated into the method of determining the identity of at least one constituent in the soot deposited on a coated substrate. In yet a further aspect of the invention, the coated substrate may be a precursor element for the production of an optical fiber.

The method of the invention results in a number of advantages over known techniques. The invention facilitates identifying the material deposited on the substrate, as well as, the concentration of the deposited material during the CVD process. This is the first time that the material deposited on a substrate and its concentration are able to be determined during depositing. This invention enables the CVD process to be integrated into a closed-loop control process. The invention also includes the advantage of determining the thickness of the substrate as well as the thickness of each layer of soot deposited on the substrate. The invention also has the advantage of a virtually non-contact measurement method so that significant perturbations to the CVD process are not generated by contact of the measurement device with the substrate during deposition. This may also be known as an untouchable measurement method. The invention has particular advantage for use in the closed-loop control system to more precisely manufacture a percursor element to produce an optical fiber.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIG. 4 is a cross sectional view along line 4—4 of FIG. 2.

DETAILED DESCRIPTION OF THE PREFERRED EMBODIMENTS

Figure 1:
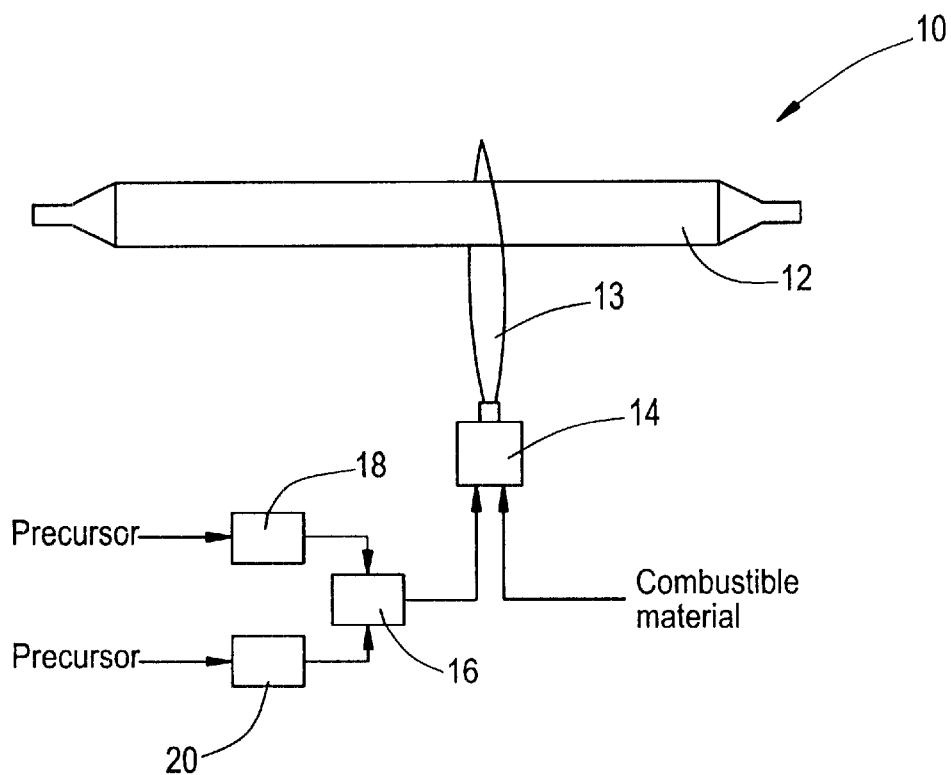
FIG. 1 is a schematic view of the conventional method to apply a soot to a blank to form an optical fiber precursor element.

Reference will now be made in detail to presently preferred embodiments of the invention. Wherever possible, the same reference numbers will be used throughout the drawings to refer to the same or like parts. Reference numerals, which are same throughout the FIGS. 1–6, indicate the same elements.

FIG. 1 is a schematic view of a conventional OVD process for manufacturing an optical fiber soot precursor element generally represented by reference numeral 10. In the process a soot is deposited on an optical fiber soot precursor element 12. The soot precursor element 12 could be, for example, a core region of soot material, which may be consolidated and drawn into a smaller diameter to form core cane, as is known in the art. Core cane may also be known as a rod. Alternatively, the soot precursor element 12 could be a complete optical fiber preform soot element, which only needs to be consolidated to be a completed optical fiber.

Desired reactants are formed by heating selected precursors in a flame 13 of a deposition burner 14. Typical precursors consist of, for example, silicon tetrachloride, germanium tetrachloride, and oxygen. The flame 13 may be produced by any known combustible material. A common gas mixture used to produce the flame 13 is oxygen and methane. Other suitable gas mixtures include air and methane, air and hydrogen and oxygen and hydrogen. The invention is not limited to anyone of the aforementioned gas mixtures. Before entering the burner 14, the precursors are mixed in a gas mixer 16. The flow of the precursors into the gas mixer 16 is controlled by a plurality of mass flow controllers 18 and 20. Preferably, the mass flow controllers 18 and 20 will dispense the precursors under the condition of laminar flow.

The present invention has applications in various CVD processes. The invention is applicable to most CVD processes in which a substrate is coated. One example of an application of the invention is the process of manufacturing a high purity fused silica glass. The invention is also applicable to applying a coating to a substrate, an optical fiber preform, an optical fiber core cane, or a glazing. Preferably, the invention may be applied to the manufacture of optical fibers. The applications of the invention are not limited to the aforementioned examples. The invention preferably incorporates laser induced breakdown spectroscopy ("LIBS") into the CVD process to monitor the progress of the soot deposition.

The present invention determines the concentration of a constituent in a soot deposited on a substrate, preferably on-line, real-time, and with layer-by-layer measurement of constituent concentration. The constituent may also be referred to as a material, dopant, or any other term to define one element of a compound. Upon learning the identity of a constituent and its concentrations, the molecular composition of the sample can be determined.

More specifically, the LIBS analytical technique utilizes a high pulsed laser to vaporize a small volume of matter on the surface of a substrate, preferably a glass or soot optical fiber preform, to be analyzed. The small volume of material is typically 100 $\mu$m in diameter by 1 $\mu$m thick. Preferably, the laser is a high power laser. The emission spectrum from the hot plasma is analyzed to determine the elemental composition of the vaporized material. The emission spectrum is typically located in the UV range of wavelengths. However, the emission spectrum may also be found in either the visible or near IR wavelength ranges.

Forming the plasma introduces energy into the vaporized material. Vaporizing the material disassociates the molecular bond, which combine the elements that form the compound vaporized. The elements are energized to an excited or ionized state. When the elements become sufficiently ionized, they return to their ground state by a decay process known as fluorescence. In this decay process, the elements emit photons of energy, i.e., fluorescent emissions. This emission may also be referred to as the production of an incandescent light. The various wavelengths included in the emission may be analyzed to determine the identity of the elements in the vaporized material. In general, the intensity of the fluorescent emissions will be proportional to the concentration of the element in the soot, as well as the amount of soot deposited. Accordingly, the invention uses these fluorescent emissions and determines the identity and concentration of an element based on the detected fluorescent emissions.

The invention may use the LIBS technique to determine constituents at a concentration level of ppm, especially metals and semi-conductors. Elements which are readily identifiable by this invention include, but are not limited to, silicon, germanium, oxygen, sodium, potassium, fluorine, and erbium. Reference is made to U.S. patent application Ser. No. 08/582,787, filed Jan. 4, 1996, and to the article *The Detection of Contaminants on Electronic Microcircuit Substrates by Laser Spark Emission Spectroscopy*, printed December, 1991 and submitted for publication in the Journal of Applied Spectroscopy, which are incorporated herein by reference as though fully set forth in their entirety, for a more detailed explanation of a LIBS device and LIBS technology.

Figure 3:
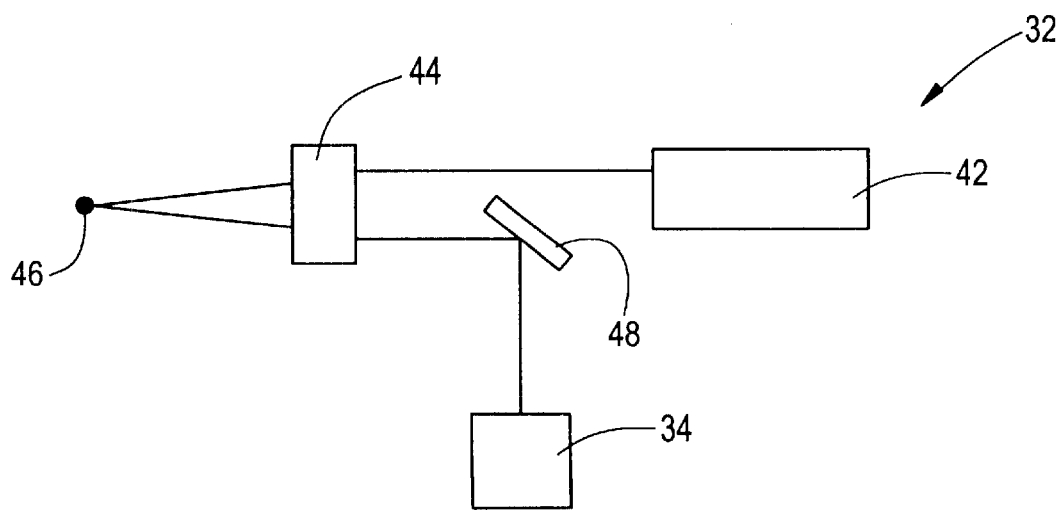
FIG. 3 is a schematic view of an embodiment of a laser induced breakdown spectroscopy device in accordance with the invention.
Figure 2:
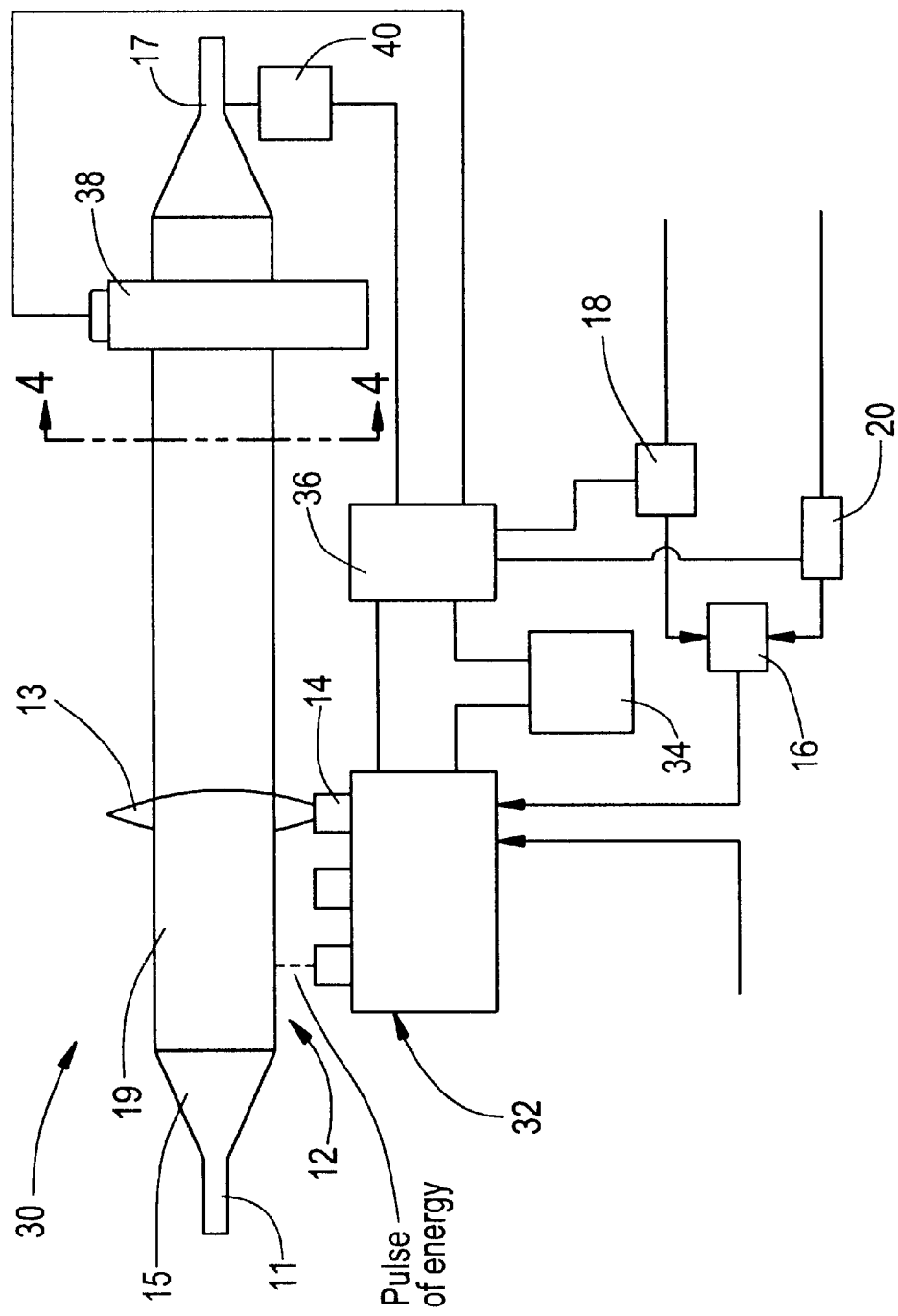
FIG. 2 is a schematic view of an embodiment of an apparatus that can be used in a method according to the present invention.

FIGS. 2 to 4 illustrate a preferred embodiment of a closed loop control apparatus 30 according to the present invention for determining an identity and a concentration of a constituent on a surface 19 of a substrate, preferably a glass or the soot precursor element 12 on a mandrel 11. The substrate is not limited to a circular shape as shown in FIG. 2. For example, the substrate may also be planar or rectangular. In alternate embodiment, the invention may used to determine the identity and concentration of a constituent on a solid substrate, such as a glass substrate.

Besides including the elements discussed in FIG. 1, the preferred embodiment includes a pulse energy source 32. The pulse energy source 32 may be integral or attached to the deposition burner 14. The pulse energy source 32 may also be separate from the burner 14. The preferred embodiment also includes an analysis element 34 and a controller 36. The analysis element 34 is typically a spectrometer. A spectrometer analysis element allows the apparatus 30 to detect the identity and concentration of various elements that make up the soot of the precursor element. If the detection of only one particular element is desired, the analysis element 34 may be a filter. However, the invention is limited to the use of a spectrometer or a filter. The controller 36 can be a computer or any other suitable type of controller. The preferred embodiment may also optionally include a thickness-parameter-measuring device 38 and a weight-measuring device 40. The thickness-parameter-measuring device 38 will be discussed during the discussion of FIG. 4.

The weight-measuring device 40 measures the weight of the soot precursor element 12 and provides a corresponding signal to the controller 36. A preferred weight-measuring device 40 includes a resistance load cell connected to one end 17 of the mandrel 11 upon which the soot precursor element 12 is formed. The other end of the mandrel 15 can be chucked to a drive motor (not shown).

The precursor element weight is recorded continuously during soot laydown. Averaging the individual load cell readings acquired during a precursor element rotation or an integral number of rotations eliminates variations due to precursor element runout. Synchronizing weight acquisition with precursor element traverse location accommodates variations due to precursor element traverse location. In other words, although weight measurements are preferably continuous, an identifier or flag is associated with the starting point of pertinent weight measurements for each traverse, and the starting point is the same in each traverse. Precursor element weight at a given segment is the average of these synchronized, averaged readings. Weight of a segment is the weight gain observed since the previous segment.

The pulse energy source 32 is shown in more detail in FIG. 3. The pulse energy source 32 is preferably a LIBS device. The source 32 includes a laser 42. Preferably the laser is a Nd:YAG Laser, however, the invention is not limited to this type of laser. One example of a suitable laser is a laser which emits a pulse of energy that may be focused to generate a plasma at a heat of about 1500 deg. Kelvin or more. Preferably, the source 32 can emit energy at a rate of a plurality of pulses per second.

A lens 44 focuses the pulse of energy emitted from the laser 42. Preferably, the lens 44 is a double convex lens. The invention is not limited to the use of a double convex lens. The double convex lens has the advantage of focusing the pulse of energy toward a predetermined point 46 on the precursor element 12 to generate the plasma and to transmit the photon created toward the analysis element 34. The lens 44 may also be referred to as a beam splitter.

Alternatively, a plurality of lens may be used to focus the energy pulse toward the predetermined point 46 on the precursor element 12 and to transmit the photon toward the analysis element 34. In this embodiment one lens would focus the energy pulse and a second lens, or a plurality of lenses, would transmit the photon to the analysis element 34.

The source 32 further includes a mirror 48 to reflect the photon to the analysis element 34. Any type of mirror with the proper heat stability and reflective properties may be used. Depending on the configuration of the energy source 32 and the analysis element 34, the mirror 48 may not be needed to practice the invention.

A cross sectional view along line 4—4 of FIG. 2 of the thickness-parameter-measuring device 38 is shown in FIG. 4. The device 38 may also be used to determine the diameter of the precursor element 12. Although the thickness-parameter-measuring device 38 is shown offset to the right in FIG. 2 for ease of illustration, it preferably measures along the center portion of the soot precursor element 12. The thickness-parameter-measuring device 38 measures a thickness parameter, such as the radius or diameter, of the soot precursor element 12. As shown in FIG. 4, the thickness-parameter-measuring device 38 can be a laser shadowing micrometer that includes a source 52 that emits optical beams and a detector 54 that detects optical beams emitted by the source 52. Based on the detected optical beams, the detector 54 provides a signal to the controller 36. This information permits a thickness parameter of the soot precursor element 12 to be determined for each traverse during soot laydown. Commercially available devices that perform this function include Anritsu KL-154A and Keyence LS-5001.

Figure 5:
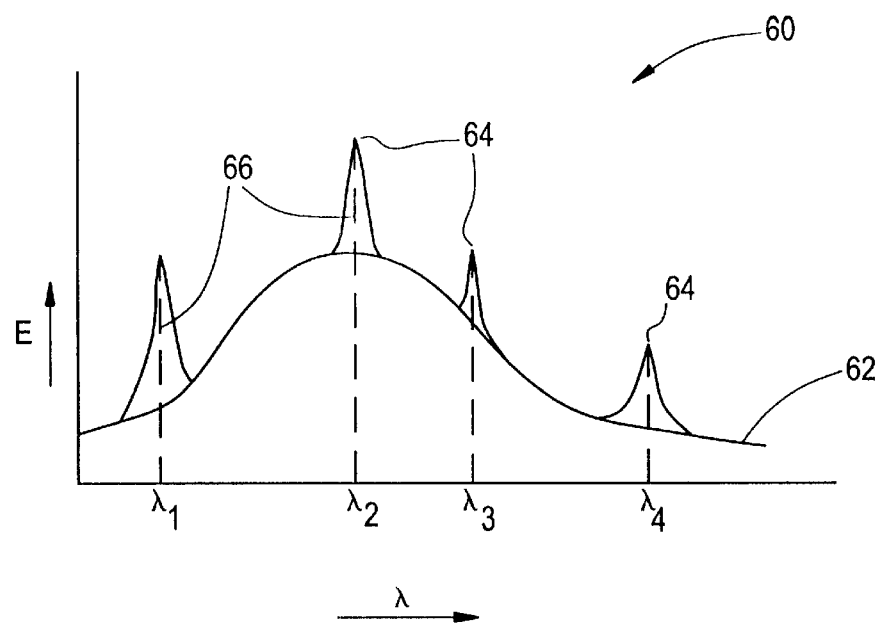
FIG. 5 is an example of a light spectrum to determine the identity and concentration of at least one material included in the soot.

FIG. 5 is an example of a light spectrum 60 of the intensity (E) of the photons emitted at a particular wavelength. The spectrum includes a curve 62 of all the light waves emitted in creating the photons. Each peak 64 indicates the presence of a specific constituent in the precursor element 12 analyzed. The actual identity of each peak 64 will depend on the numerical value of λ (lambda). Each element may be located at a particular range of wavelengths. For example the decay of a potassium (K) electron from the 4$p$ valence shell to the 4$s$ valence shell will typically appear at wavelengths between 766 nm to 770 nm. For a sodium (Na) electron, decay from the 4$d$ to 3$p$ valance shells will appear at a range of 569 nm to 590 nm and decay from the 3$d$ to 3$p$ valence shells will appear at 818 nm to 820 nm.

The amount of a particular constituent is determined from the height 66 of the peak 64. The distance 66 from the peak 64 to the curve 62 may be used to determine the amount of the element, which is represented by the peak 64.

Figure 6:
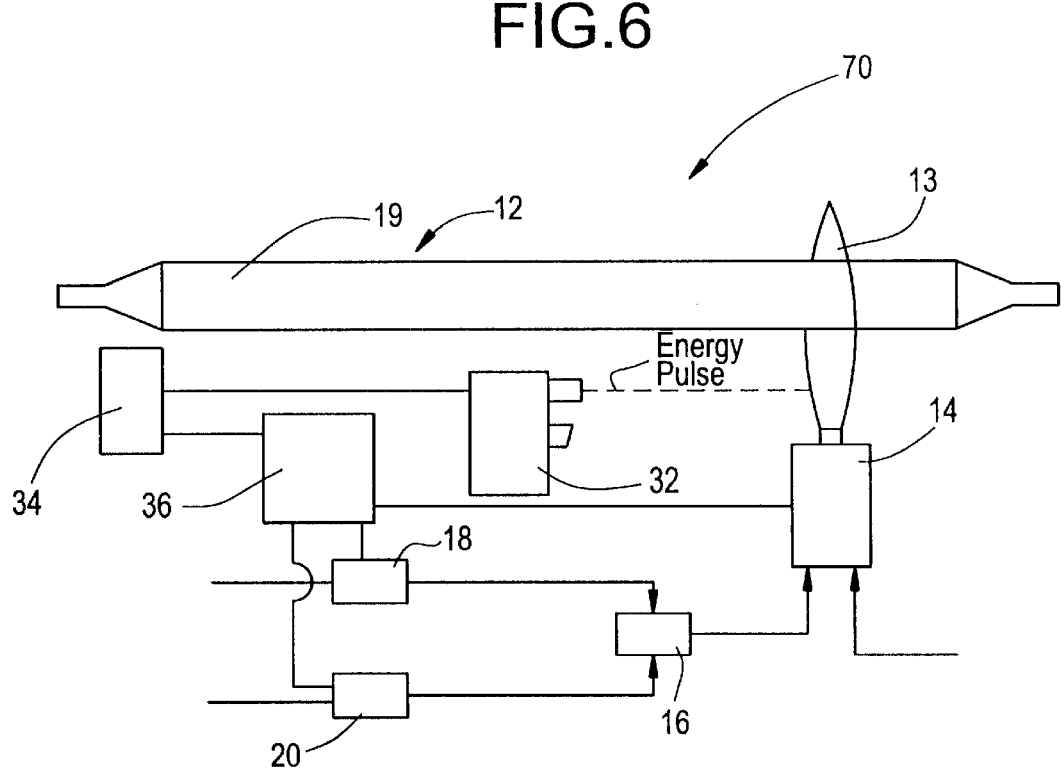
FIG. 6 is a schematic view of an embodiment in accordance with the invention to determine the identity and concentration of at least one constituent of the reactants at a predetermined point in the flame of the deposition burner.

FIG. 6 is an alternate embodiment of invention. The configuration 70 is an alternate embodiment of the apparatus 30. The configuration 70 may be used to determine the identity of a reactant in the flame 13 of the burner 14. In the configuration 70 the source 32 is detached from the burner 14. The source 32 is disposed such that the pulse of energy may be focused at a predetermined point in the flame. A plasma is generated at the predetermined point in the flame, which creates the photons to be analyzed. In all other respects the configuration 70 is the same as the apparatus 30.

Another embodiment of the invention is to combine the concepts behind the apparatus 30 and the alternate configuration 70. In this embodiment, the identity and amount on the surface 19 of the precursor element 12, as well as, the identity and amount of the reactants in the flame 13 would be analyzed. This embodiment would typically require a plurality of sources for sending a pulse of energy. Alternatively, a single source could be used which would be rotated from sending a pulse of energy toward the precursor element 12 and from sending a pulse of energy toward the flame 13.

A further embodiment of the invention includes a method of determining an identity of at least one reactant in a reactant stream of a chemical vapor deposition process for depositing a soot on a substrate. The reactant stream may be a vapor phase or liquid phase stream. The method includes the steps of sending a pulse of energy toward the reactant stream. The energy is focused to a predetermined point in the stream to thereby generate a plasma in the stream and to create a photon. The photon is detected using an analysis element. The analysis element may be a spectrometer. The identity of the constituent in the stream is determined.

The method may also include transmitting the identity and/or amount of the constituent to a controller. The identity or amount of the constituent is compared to a predetermined set of parameters. If the identity or amount of the constituent does not match at least one of the predetermined set of parameters, at least one reaction condition is altered such that the identity or amount of the constituent will match the one of the predetermined set of parameters. This embodiment of the invention may use laser induced breakdown spectroscopy to identify the constituent and its concentration. The set of predetermined parameters may typically include a list of constituents and desired amounts of each constituent, however, the set of predetermined parameters is not limited to the aforementioned.

METHOD OF OPERATION

The closed loop control apparatus 30 may be used to determine the identity and/or amount of constituents on the surface 19 of the precursor element 12 by the following method. The pulse of energy source 32 sends a pulse of energy toward the precursor element 12. The pulse of energy is focused to a predetermined point 46 on the precursor element 12. This accomplished by passing the pulse through the lens 44. The energy strikes the predetermined point 46 on the precursor element 12, thereby vaporizing a small volume of material on the surface 19 of the precursor element 12 and generating the plasma. In generating the plasma, the bonds between the elements, which make up the material vaporized disassociate and at least one valence shell electron, of each element, is excited. Upon the valence shell electron returning to its respective ground state, a photon is emitted. The photon is transmitted to the analysis element 34. The identity of each constituent vaporized may be determined. Likewise, the concentration of each constituent identified may also be determined. The volume of material vaporized is preferably disposed near either end 15 or 17 of the precursor element 12 to prevent seeding.

Once the identity and concentration of a constituent is determined, this data can be used to determine the molecular composition of the sample and likewise the object being sampled. This is especially true when the identity and concentration of a plurality of constituents is determined.

In the preferred embodiment, the identity of each constituent may be used to monitor the process of manufacturing the soot precursor element 12. In this embodiment, the identity of each constituent, and optionally its concentration, is transmitted from the analysis element 34 to the controller 36.

The controller 36 will compare the identity of each constituent and the respective concentrations to a predetermined set of parameters and concentrations. If the identity of each constituent or its respective concentration does not match the predetermined set of parameters, the controller may alter one or more reaction conditions. A non-exhaustive list of reaction conditions which may be altered include the flow rate of any of the precursors flowing into the respective mass flow controllers 18 and 20, the temperature of the flame 13 of the burner 14, or the temperature of the precursor element 12.

Optionally, the controller 36 may also be used to monitor the thickness of the precursor element 12 and/or the weight of the precursor element 12, similar to monitoring the constituents of the precursor element 12. Likewise, the controller 36 may alter the reaction conditions depending on the monitored value of the thickness or weight of the precursor element in comparison to a predetermined set conditions of thickness or weight of the precursor element.

A further embodiment of the invention may include the steps of cleaning lens 44. This is typically accomplished by passing a cleaning purge gas across the surfaces of the lens 44. One suitable type of purge gas is nitrogen. Any suitable type of inert purge gas may be used.

An additional embodiment of the invention may include cooling the various subelements of the source 32. In this embodiment, a cooling device is disposed to maintain at least the lens 44 below a predetermined maximum temperature. The cooling device may also be disposed to maintain the laser 42 and the mirror 48 below a predetermined maximum temperature. The predetermined maximum temperature for each subelement may differ.

Though the drawings and the specification describe the invention in regard to the OVD process, the invention is not limited to the OVD process. This invention may be practiced in the manufacturing of soot precursor elements by any known techniques such as, but not limited to, PCVD, PECVD, MCVD or VAD.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of determining an identity and/or amount of at least one constituent in a soot on a soot coated substrate, the method comprising the steps of:

sending a pulse of energy toward the coated substrate;

focusing the energy to a predetermined point on the substrate to thereby generate a plasma on the substrate and to create at least one photon;

detecting the photon using an analysis element; and determining the identity or amount of the constituent in the soot.

2. The method of claim 1, wherein said determining step is accomplished by laser induced breakdown spectroscopy.

3. The method of claim 1, further comprising the steps of comparing the identity or amount of the constituent to a predetermined set of parameters, and adjusting at least one reaction condition such that the identity or amount of the constituent will be altered to match at least one of the predetermined set of parameters.

4. The method of claim 1, wherein said step of sending a pulse of energy toward the substrate consists of sending the energy at a rate of a plurality of pulses per second.

5. The method of claim 1, wherein the analysis element is a spectrometer.

6. The method of claim 1, wherein said step of focusing the energy to a predetermined point is accomplished with a double convex lens.

7. The method of claim 1, wherein the substrate is an optical fiber precursor element.

8. A method of making an optical fiber soot precursor element in accordance with claim 3, wherein said parameters are selected to form a desired refractive index profile of a core region.

9. The method of claim 1, wherein said step of determining the identity and amount of a constituent in the soot includes identifying a plurality of constituents and the amount of each constituent.

10. The method as defined in claim 9, further comprising the step of determining a molecular composition of the constituents identified.

11. The method of claim 1 further comprising depositing soot on the substrate.

12. A method of determining an identity and/or amount of a at least one reactant in a flame of a chemical vapor deposition process for depositing a soot on a substrate, the method comprising the steps of:

sending a pulse of energy toward the flame; and focusing the energy to a predetermined point in the flame to thereby generate a plasma in the flame and to create at least one photon;

detecting the photon using an analysis element; and determining the identity and amount of at least one constituent in the flame.

13. The of method of claim 12, further comprising the steps of:

comparing the identity or amount of the constituent to a predetermined set of parameters; and adjusting at least one reaction condition such that the identity or amount of the constituent will be altered to match the one of the predetermined set of parameters.

14. The method of claim 12, wherein said step of sending a pulse of energy toward the flame consists of sending the energy at a rate of a plurality of pulses per second.

15. The method of claim 12, wherein the analysis element is a spectrometer.

16. The method of claim 12, wherein said step of focusing the energy to a predetermined point is accomplished with a double convex lens.

17. The method of claim 12, wherein the identity of the constituent is accomplished by laser induced breakdown spectroscopy.

18. The method of claim 13, wherein the at least one reaction condition adjusted is selected from the group consisting of reaction temperature and flow rate of at least one reactant.

19. The method of claim 12, wherein said step of determining the identity and amount of the constituent in the flame includes identifying a plurality of constituents in the flame and the amount of each constituent.

20. The method of claim 19, further comprising determining a molecular composition of the constituents identified.

21. The method of claim 12 further comprising depositing soot on the substrate.

22. A method of determining an identity and/or amount of a at least one reactant in a reactant stream of a chemical vapor deposition process for depositing a soot on a substrate, the method comprising the steps of:

sending a pulse of energy toward the reactant stream;

focusing the energy to a predetermined point in the stream to thereby generate a plasma in the stream and to create at least one photon;

detecting the photon using an analysis element; and determining the identity or amount of at least one constituent in the stream.

23. The of method of claim 22, further comprising the steps of:

comparing the identity and or amount of the constituent to a predetermined set of parameters; and adjusting at least one reaction condition such that the identity of the constituent will be altered to match the one of the predetermined set of parameters.

24. The method of claim 22, wherein said determining the identity and/or amount of the constituent is accomplished by laser induced breakdown spectroscopy.

25. The method according to claim 22 further comprising depositing soot on the substrate.

26. A method of forming an optical fiber preform comprising:

depositing soot on to a substrate;

sending a pulse energy toward a target, wherein the target comprises at least one selected from soot deposited on the substrate, a flame of a chemical vapor deposition process for depositing the soot, a reactant stream, and combinations thereof;

focusing the energy to a predetermined point on the target to thereby generate a plasma on the target and to create at least one photon;

detecting the photon using an analysis element; and determining the identity or amount of at least one constituent of the target.

27. The method of claim 26 wherein said determining step comprises laser induced breakdown spectroscopy.

28. The method of claim 26 further comprising the steps of comparing the identity or amount of the constituent to a predetermined set of parameters, and adjusting at least one reaction condition such that the identity or amount of the constituent will be altered to match at least one of the predetermined set of parameters.

* * * * *